United States Patent [19]
Corn

[11] Patent Number: 5,370,110
[45] Date of Patent: Dec. 6, 1994

[54] ANESTHETIC SCAVENGING HOOD

[75] Inventor: Stephen B. Corn, Boston, Mass.

[73] Assignee: Children's Medical Center Corporation, Boston, Mass.

[21] Appl. No.: 938,366

[22] Filed: Aug. 31, 1992

[51] Int. Cl.$^5$ .............................................. A62B 17/04
[52] U.S. Cl. ......................... 128/201.22; 128/205.12; 128/910
[58] Field of Search ...................... 128/201.22, 201.24, 128/202.12, 203.12, 205.19, 205.26, 201.29, 910, 205.12

[56] References Cited

U.S. PATENT DOCUMENTS

| | | | |
|---|---|---|---|
| 2,742,900 | 4/1956 | Giorgio et al. | 128/201.23 |
| 3,604,416 | 9/1971 | Petrahai et al. | 128/201.25 |
| 3,747,599 | 7/1973 | Malmin | 128/201.29 |
| 4,019,508 | 4/1977 | Der Estephanian et al. | 128/201.29 |
| 4,022,200 | 5/1977 | Jonson . | |
| 4,055,173 | 10/1977 | Knab | 128/201.29 |
| 4,444,183 | 4/1984 | Heckendorn | 128/205.26 |
| 4,620,538 | 11/1986 | Koegel et al. | 128/205.26 |
| 4,836,197 | 6/1989 | Rohling et al. | 128/201.23 |
| 4,949,714 | 8/1990 | Orr | 128/200.24 |
| 5,046,492 | 9/1991 | Stackhouse et al. | 128/205.19 |

OTHER PUBLICATIONS

Ralph D. Swenson, *Scavenging of Dental Anesthetic Gases*, J. Oral Surg. 34:207–214, Mar. 1976.
A. P. Adams, *A Scavenging System and Expiratory Valve for Use in Out-Patient Dental Anesthesia*, British Dental Journal, Jul. 20, 1976.
Paul D. Davis, et al. *The Brown Nasal Mask*, British Dental Journal 1979, pp. 246–248.
D. Moves, et al. *Comparison of Three Anaesthetic Scavenging Devices Using Cuffed and Noncuffed Nasal Endoctracheal Tubes During Dental Anaesthesia*, SA Medical Journal, Feb. 7, 1981, pp. 180–182.
Anna-Lena Hallonsten, *Nitrous Oxide Scavenging in Dental Surgery*, Swed. Dent. J. 6:203–213 and 6:215–233, (1982).
Ingrid Anderson-Wenckert, et al. *Anevac-D, A New System for Close Scavenging of Anesthetic Gases in Dental Practice*, Dept. of Anaesthesia, University of Sweden, May 4, 19889.
E. R. Young, et al. *A Scavenging System Developed for the Magill Anesthetic Circuit for Use in the Dental Office*, Anesth, Prog. 37:252–257, 1990.

*Primary Examiner*—Edgar S. Burr
*Assistant Examiner*—Aaron J. Lewis
*Attorney, Agent, or Firm*—Thomas J. Engellenner; William C. Geary, II

[57] ABSTRACT

An anesthesia scavenging hood is adapted to fit over the head of a surgical patient and to prevent the contamination of operating rooms with waste anesthetic vapor and nitrous oxide gas. The hood enables placement of an endotracheal tube or other breathing or anesthesia circuit into the patient's airway. The hood may be sealed about the endotracheal tube and about the patient. The hood also includes a port having disposed therein a suction tube which communicates waste vapor and gas out of the hood and outside of the operating room with the aid of a vacuum source.

8 Claims, 5 Drawing Sheets

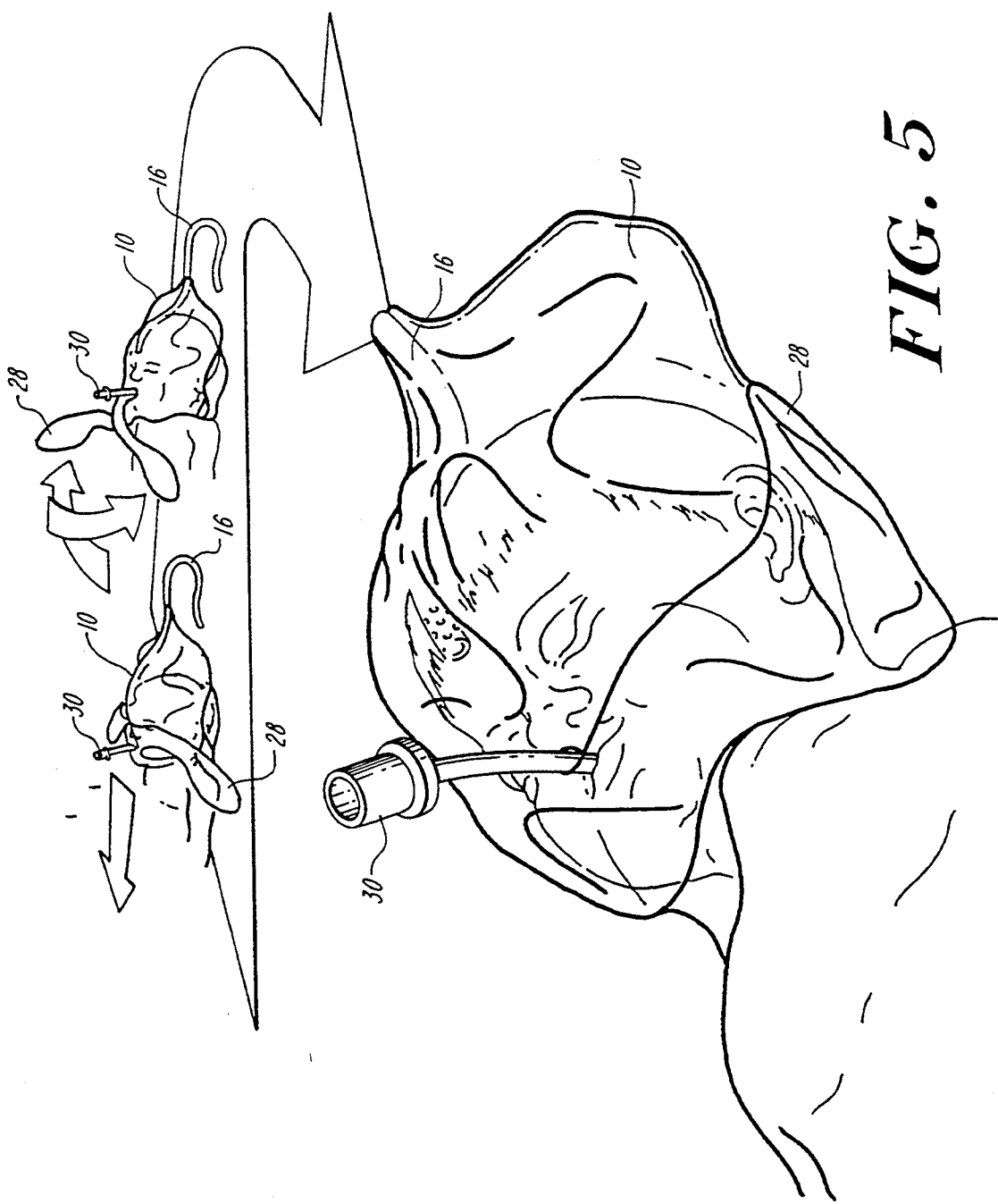

ANESTHETIC SCAVENGING HOOD

BACKGROUND OF THE INVENTION

The present invention relates to a scavenging device that prevents the release of anesthetic gas into the environment of an operating room.

Surgical procedures frequently require the application of general anesthesia to a patient undergoing surgery or another medical procedure. The anesthetic is often delivered through an uncuffed endotracheal (ET) tube. Such a method of delivering anesthetic gas is known to result in contamination of the operating room environment with potentially harmful levels of volatile anesthetic vapor and nitrous oxide gas due to leakage around the ET tube. Studies have suggested that chronic exposure to trace levels of anesthetic gas is harmful to operating room personnel. Additionally, acute exposure of operating room personnel to such agents often leads to complaints of headache, fatigue, and irritability. Accordingly, means have been sought to eliminate or minimize the presence of waste anesthesia in operating rooms without compromising the safe administration of anesthesia.

The mere venting or conditioning of air within an operating room is not considered to be effective to adequately purge the room of any leaked anesthesia gas.

Certain devices have been designed to enclose a patient's head within a hood or mask while delivering a breathing gas and an anesthesia gas into the interior of the hood. Devices such as those disclosed in U.S. Pat. Nos. 2,742,900 (Giorgio et al.), 4,949,714 (Orr), and 4,444,183 (Heckendorn) typically are used to provide an enclosed space over the patient through which to deliver anesthetic to the patient. These devices generally allow excess anesthetic to be vented directly into the environment of the operating room. In some instances, such as disclosed in the Orr patent, a vacuum port is adjacent to, but not in direct contact with, the exhaust port. Thus, anesthesia gas is emitted into the operating room environment before it is evacuated through the vacuum. Although somewhat effective, such a device may well leave trace amounts of waste anesthesia gas in the operating room, potentially affecting the health of the medical staff within the room.

Accordingly, it would be advantageous to provide anesthesia delivery devices and methods of delivering anesthesia that eliminate or greatly minimize the amount of waste anesthesia gases to which operating room personnel are exposed.

It is thus an object of the invention to provide a device which enables the safe administration of anesthesia while venting any waste anesthesia gas out of the operating room environment. Another object is to provide a waste anesthesia scavenging device which encloses a portion of the patient's head and prevents the escape of any waste anesthesia into the operating room environment. A further object is to provide a waste anesthesia scavenging device which effectively removes waste anesthesia from the operating room environment while enabling general anesthesia to be delivered through traditional techniques. It is also an object of the invention is to provide a method of safely and effectively preventing the emission of waste anesthesia and other gases into an operating room environment. Other objects of the invention will be apparent upon reading the disclosure which follows.

SUMMARY OF THE INVENTION

The anesthesia scavenging device of the present invention preferably is in the form of a hood or shroud which encloses at least a portion of a patient such as the patient's head or face. The device typically is in the form of a bag or other gas impermeable, flexible fabric which is of sufficient size to enclose a patient's head. The device may take other forms as well, such as cup—or bowl shaped—objects which enclose a portion of the patient's head such as the nose and mouth. Preferably a bottom portion of the device or hood is open to allow for placement over a patient's head. The bottom portion of the hood can also be adapted to be selectively fastened about a patient in such a way that the hood is closed without jeopardizing the safety of the patient.

The scavenging hood preferably has at least one exhaust port which engages a length of suction tubing. Preferably, the tubing extends into and protrudes from the hood. An external, protruding portion of the tubing mates to a section of suction hose which, in turn, is connected to a vacuum source. In one embodiment the inner portion of suction tubing terminates approximately adjacent the patient's face and includes a plurality of perforations adjacent to its terminal end through which gas to be exhausted may enter the tube.

As noted, the suction hose preferably connects to a standard wall-mounted suction source which is present within operating rooms and which is adapted to vent the gas out of the room and/or building. Alternatively, the suction hose can communicate with a portable suction unit which likewise is adapted to create a suction force and to convey exhausted gases out of the operating room. The magnitude of the suction force can be regulated directly by the suction source or by a device adjacent the suction hose (such as a roller clamp) which restricts the flow within the hose.

There is also provided within the hood an opening or port which allows an ET tube to exit from the hood. Optionally, the scavenging hood may have a third port or opening adapted to communicate with a device which delivers a heated humidified air over the patient's face.

The anesthesia scavenging hood of this invention is suitable for use with human surgery as well as with veterinary surgery. Accordingly, the term "patient" refers to both humans and animals.

BRIEF DESCRIPTION OF THE DRAWINGS

FIG. 5 is a schematic view illustrating the use of the scavenging hood of the invention with a patient.

DETAIL DESCRIPTION OF THE INVENTION

Figure 1:
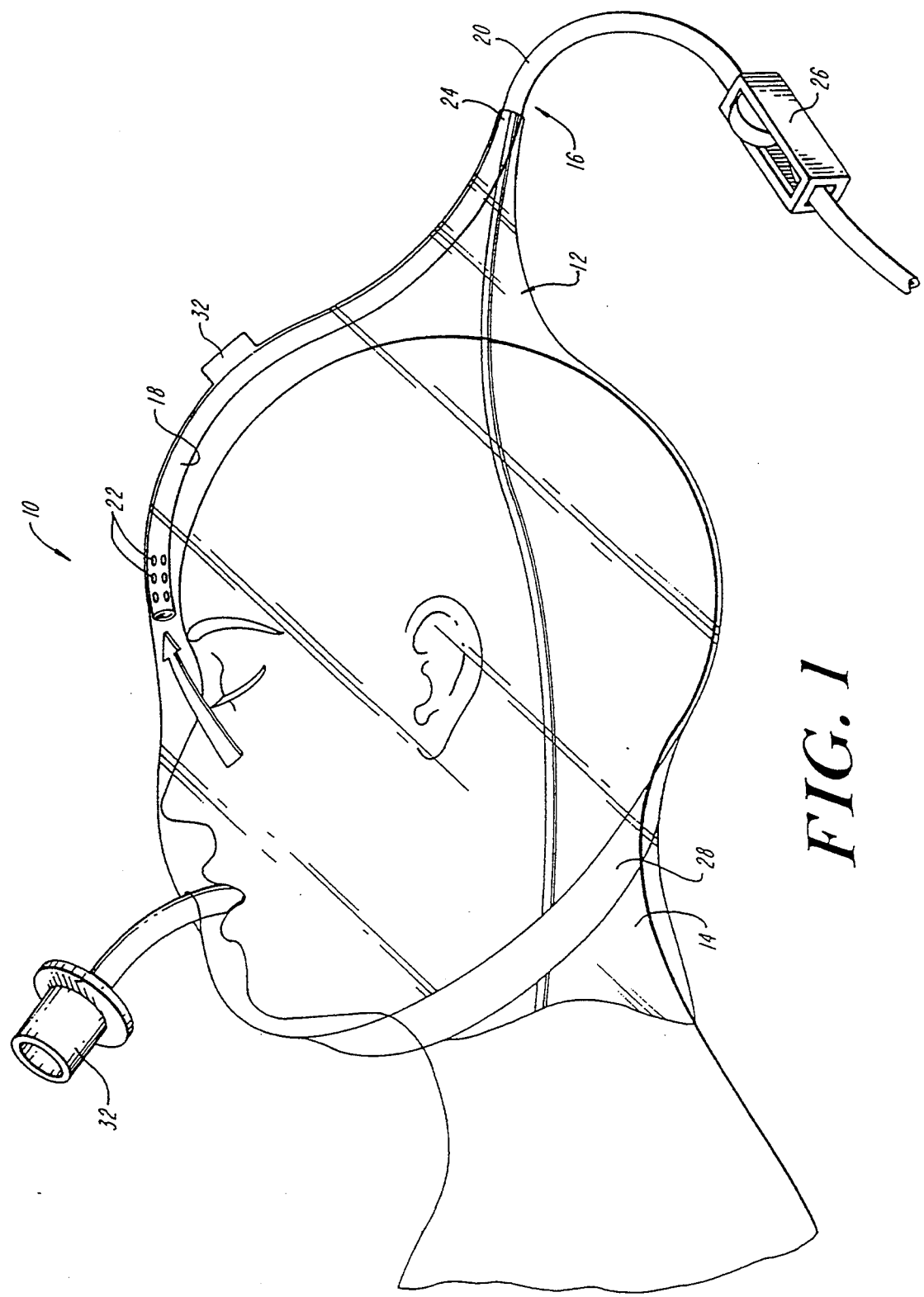
FIG. 1 is a schematic view illustrating the anesthetic scavenging hood of the invention encompassing the head of a patient.
Figure 2:
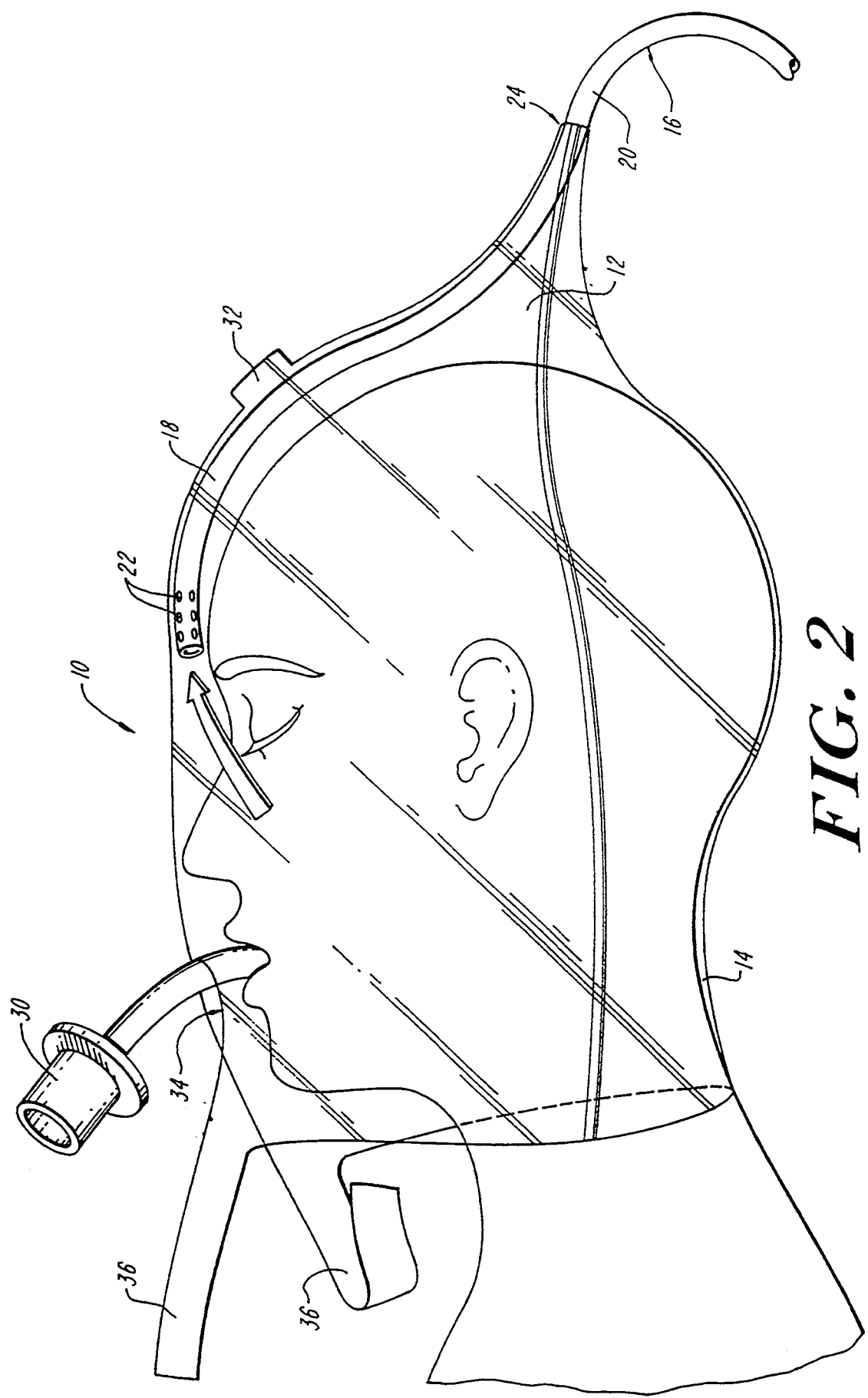
FIG. 2 is a side view, partially cut away, of the scavenging hood of the invention.

FIGS. 1 and 2 illustrate the anesthesia scavenging hood 10 of the present invention enclosing a patient's head. The scavenging hood 10 has a top portion 12 and a bottom portion 14. A suction tube 16 preferably enters the hood through a top portion thereof and extends within the interior of the hood, terminating at a position adjacent the patient's face as shown in FIGS. 1 and 2. The bottom portion of the hood, at a location adjacent the patient's mouth, includes a slit or opening 34 which accommodates and seals about an endotracheal tube 30 or other breathing or anesthesia circuit means for delivering anesthesia to a patient. In addition, the bottom portion of the hood includes flaps 28 or release tape 26 which enable a loose but effective seal to be created about the patient's neck.

The suction tube 16, as illustrated in FIGS. 1 through 4, preferably includes an external portion 20 and an internal portion 18. The suction tube 16 preferably enters the hood through port 24 disposed on the top portion of the hood. Preferably, the port 24 is heat sealed about the tube to create a substantially leak proof seal. In addition the interior portion 18 of tube 16 preferably is secured to the interior surface of the hood and terminates at a location substantially adjacent the patient's face. The interior portion 18 of tube 16 preferably has an open distal end with a plurality of perforations 22 disposed in the tube adjacent its distal end to facilitate evacuation of gases from within the hood. The exterior portion 20 of tube 16 may include a clamping device such as roller clamp 26, which can be used to control the magnitude of the vacuum force by restricting flow within the tube. The exterior portion 20 of tube 16 preferably attaches to a suction hose (not shown) which is in communication with a vacuum source or other means of creating a suction force for removing gases from within the hood.

Although tube 16 preferably enters the interior of hood 10, other embodiments may utilize a suction tube which does not extend into the interior of the hood but instead is flush with the surface of the hood. Also, the port 24 may be positioned elsewhere on the hood.

As noted, the hood 10 includes a bottom portion 14 adapted to close about a patient, for example about the patient's neck, and to receive an endotracheal tube 30. In one embodiment, illustrated in FIG. 2, the bottom portion of the hood 10 includes a V-shaped split 34 which forms an exit port for endotracheal tube 30. The split 34 may be closed about the tube and about the patient's neck through a fastening mechanism such as strips of release tape 36. The seal created about endotracheal tube 30 and the patient's neck need not necessarily be airtight. While air may be permitted to enter the interior of the hood from openings adjacent the endotracheal tube or the patient's neck, air is withdrawn from within the hood through tube 16 with sufficient force to prevent any leakage of anesthesia gas from openings about the endotracheal tube or the patient's neck.

Figure 3:
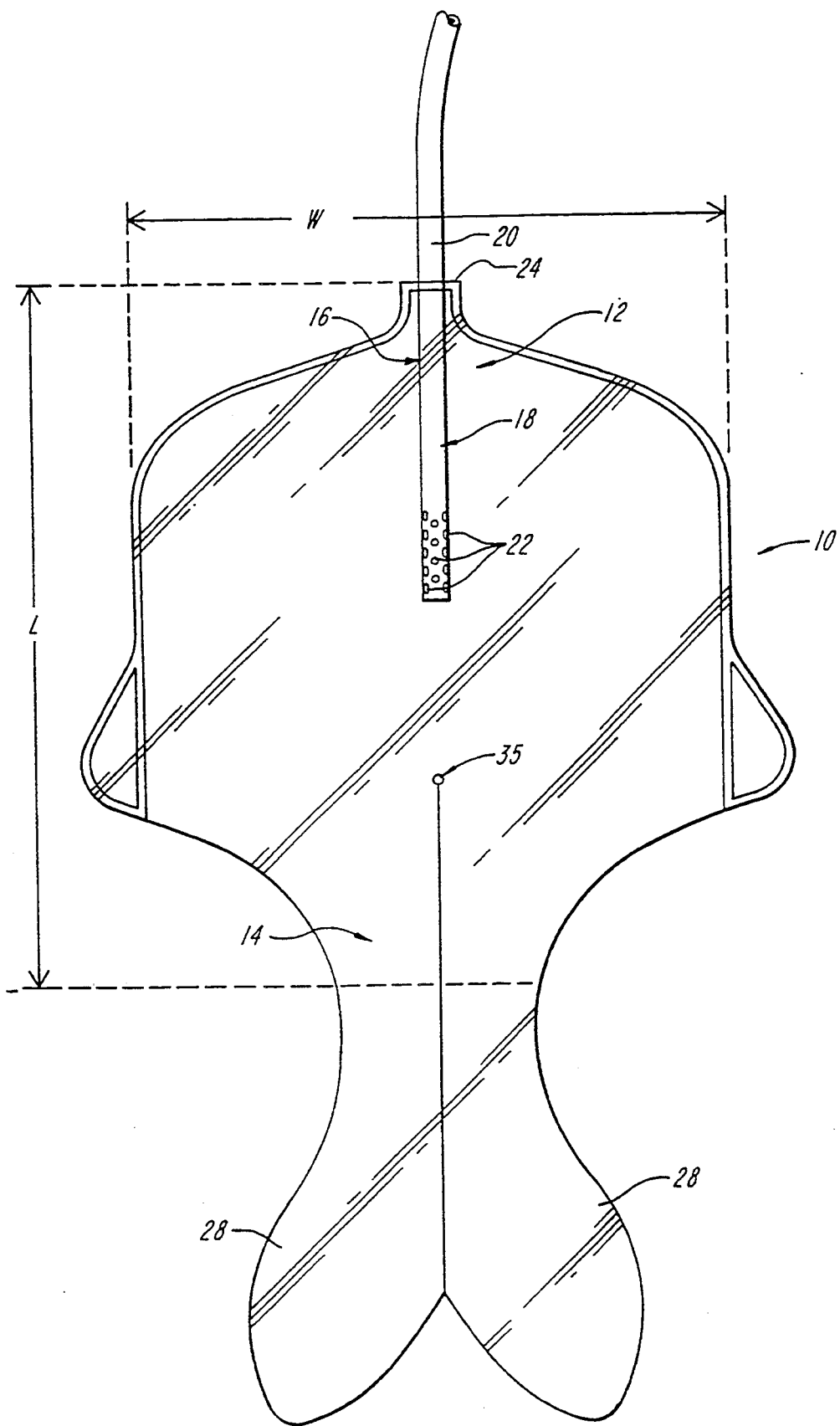
FIG. 3 is a top view of an anesthesia scavenging hood of the present invention.
Figure 4:
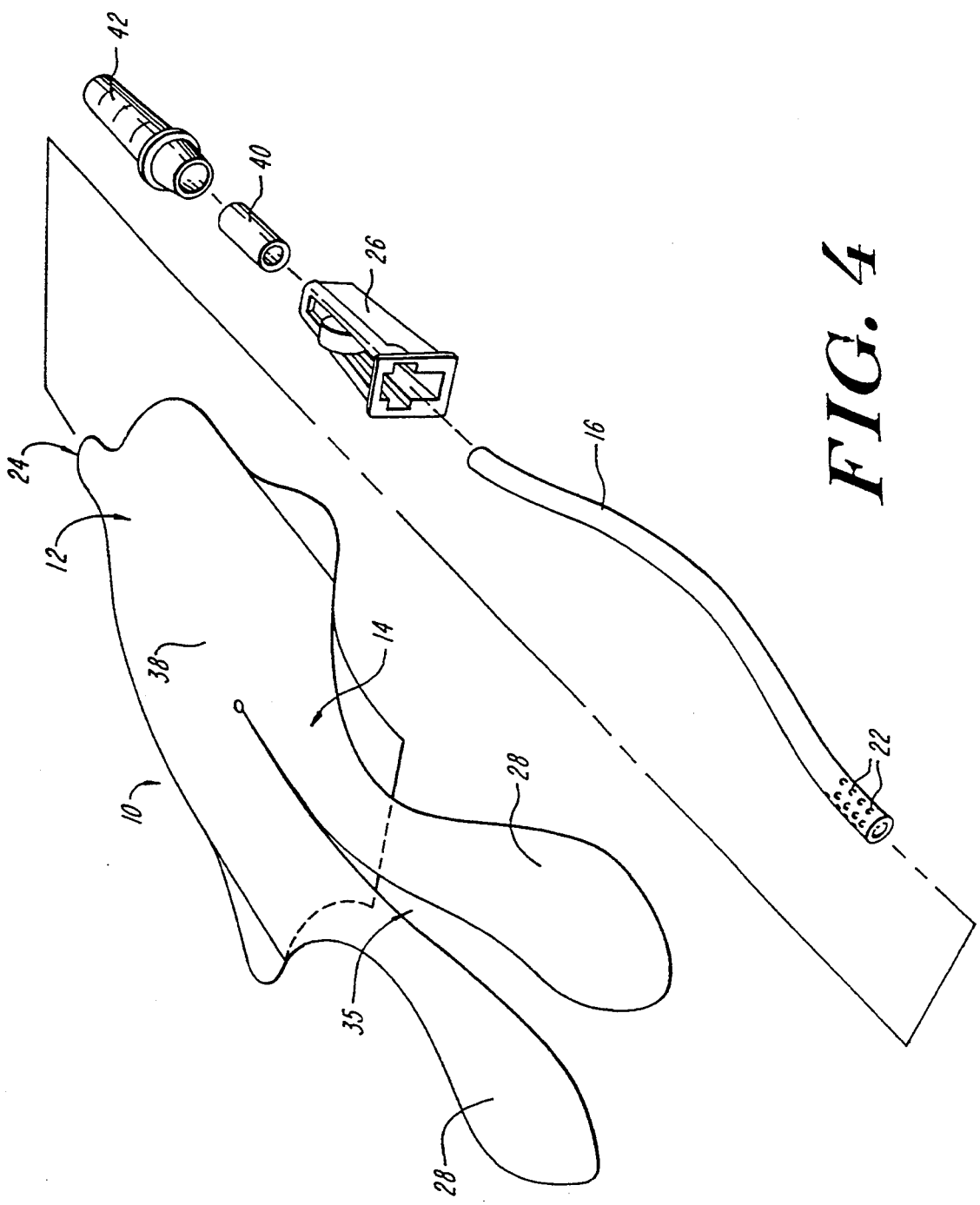
FIG. 4 is a schematic, exploded view illustrating unassembled components which form the scavenging hood of the invention.

In an alternative embodiment illustrated in FIGS. 1, 3 and 4, the front facing, bottom portion of the hood includes elongated flaps 28 which are separated from each other. The hood is positioned over the patient's head to allow the endotracheal tube 30 to exit the hood through split 35 which separates the flaps 28 from each other. The flaps 28 may then be wrapped around the patient's head to create an effective degree of sealing about the endotracheal tube and about the patient's neck. Any leakage of anesthesia gas through openings in the hood adjacent to the endotracheal tube or the patient's neck should be prevented by the suction force applied through tube 16.

In a preferred embodiment, as illustrated in FIGS. 1 and 4, the top surface of the hood adjacent a patient's face, includes score lines 38 and an attached emergency release tab 32 to facilitate rapid removal of the anesthesia hood from a patient's head. In the event of an emergency, the hood may be removed quickly and easily by simply grasping the release tab 32 and exerting pressure thereon in order to open the hood along the score lines.

The hood 10 preferably is manufactured from a gas impermeable transparent plastic film such as polyvinyl chloride or other suitable polymers well known in the art. The material preferably has a thickness in the range of about 2 to 6 mils. As described above, the hood 10 is open at a bottom portion 14 thereof, and a port 24 disposed in the top portion 12 of the hood is sealed about tube 16. The hood may be manufactured by a variety of techniques well known in the art.

The dimensions of the hood can vary to accommodate human and animal patients alike. Versions of the hood 10 suitable for use with humans may be sized for use with neonates, infants, children, and adults.

FIG. 3 illustrates an embodiment of the invention suitable for use with infant patients. Exemplary dimensions of such a scavenging hood 10 are such that the width (W) ranges from 7–10 inches and the length (L) range from 15 to 20 inches. The length of flaps 28 is approximately 6 to 8 inches. Hoods suitable for use with children and adults are of greater dimensions. One of ordinary skill in the art can readily ascertain the dimensions appropriate for a given patient class.

Suction tube 16 preferably is manufactured from a suitable substantially rigid polymer such as polyvinyl chloride. The outer diameter of tube 16 is preferably in the range of 0.15 to 0.25 inches, while the inner diameter ranges from 0.10 to 0.15 inches. As noted, the inner portion 18 of tube 16 preferably is secured to the inner surface of the hood 10 by heat staking or by other known techniques.

The length of the tube 16, as well as the length of the inner portion 18 and outer portion 20 may vary depending upon the requirements of a given application. By way of example, the entire length of tube 16 can be about 10 to 18 inches, the length of inner portion 18 can be about 4 to 6 inches, and the length of outer portion can be about 6 to 12 inches.

The scavenger hood of the invention is adapted to be used with conventional wall-mounted suction devices which are well-known and commonly present in operating rooms. Such as system typically vents withdrawn gas out of both the operating room and the hospital. Alternatively, the hood may be used with a portable suction device which is similarly adapted to create a vacuum force and to vent withdrawn gases out of the operating room.

The magnitude of the vacuum force used to withdraw gases from within hood 10 preferably is in the range of 5 to 22 in. Hg., and more preferably about 5 to 15 in. Hg.. In addition, the flow rate of the withdrawn gases through tube 16 may range from about 1 to 5 liters per minute. One skilled in the art will readily be able to ascertain the magnitude of vacuum force and flow rate which is suitable for a given patient during a given surgical procedure. Vacuum force and flow rate may be controlled by means associated with the vacuum source, and/or by devices which affect flow rate by selectively restricting the diameter of the outer portion 20 of tube 16.

As noted, the scavenging hood of the present invention is useful in that it prevents the escape of anesthetic vapor gas and nitrous oxide into the environment of the operating room. During a surgical procedure, as illustrated in FIG. 5, the patient is intubated in the usual manner, and the hood 10 is placed about the patient's head and sealed, as described above, about the patient's neck and the intubating tube. Tube 16 is connected to a suitable vacuum source, and the vacuum source is activated. As anesthesia gas is delivered to the patient through the endotracheal tube, any leaked vapor or gas which is present within the environment of the hood is removed from the hood through tube 16 and is vented outside of the operating room. In addition to preventing the contamination of an operating room with waste anesthetic vapor and nitrous oxide gas, the hood 10 also is beneficial in that it conserves the patient's body heat during surgical procedures.

Various modifications may be made to the present invention without departing from the intended scope thereof.

What is claimed is:

1. A scavenging device, comprising:
   an enclosure means for placement over at least a portion of a patients head, the enclosure means having an open bottom portion, and means to close said open bottom to substantially seal about the patient's neck, said enclosure being formed of a gas impermeable, plastic film;
   a first opening substantially in the form of a V-shaped slit disposed in the enclosure and including an anesthesia circuit fitting directly communicating with a patient's airway; and
   a second opening in the enclosure, and a conduit means sealingly engaged with the second opening for directly communicating a vacuum force to the interior of the enclosure means and a third opening in the enclosure means and in communication with a means for delivering heated, humidified air to the interior of the enclosure means.

2. The device of claim 1 further comprising a second opening disposed in the enclosure means wherein the second opening is adapted to be sealingly engaged with the conduit means.

3. The device of claim 1 further comprising a fastening means for selectively closing the first opening about the breathing or anesthesia circuit fitting and the bottom portion of the enclosure means about the patient.

4. The device of claim 1 wherein the conduit means is of a length sufficient to extend within the enclosure means and to protrude from the enclosure means, wherein the portion of the conduit extending within the interior of the enclosure means is affixed to an inner surface of the enclosure means.

5. The device of claim 4 wherein a terminal end of the portion of the conduit means extending within the enclosure means also includes a plurality of perforations.

6. The device of claim 5 wherein the perforations are disposed in the conduit means at a position approximately adjacent to the patient's face.

7. The device of claim 5 wherein the portion of the conduit means which protrudes from the enclosure means is adapted to connect to suction tubing that communicates with a vacuum source.

8. The device of claim 1 wherein a means for selectively closing the first opening about an anesthesia circuit fitting and about the patient comprises at least one strip of release tape.

* * * * *